US008546607B2

(12) United States Patent
Garg et al.

(10) Patent No.: US 8,546,607 B2
(45) Date of Patent: Oct. 1, 2013

(54) CROSS-COUPLING OF PHENOLIC DERIVATIVES

(75) Inventors: Neil K. Garg, Los Angeles, CA (US); Kyle W. Quasdorf, Los Angeles, CA (US); Xia Tian, Boston, MA (US)

(73) Assignee: The Regents of the University of California, Oakland, CA (US)

( * ) Notice: Subject to any disclaimer, the term of this patent is extended or adjusted under 35 U.S.C. 154(b) by 165 days.

(21) Appl. No.: 12/889,765

(22) Filed: Sep. 24, 2010

(65) Prior Publication Data

US 2011/0077406 A1    Mar. 31, 2011

Related U.S. Application Data

(60) Provisional application No. 61/245,752, filed on Sep. 25, 2009.

(51) Int. Cl.
*C07F 5/02* (2006.01)
*C07F 9/02* (2006.01)

(52) U.S. Cl.
USPC .................. 562/7; 568/17; 568/706; 558/48; 558/72

(58) Field of Classification Search
USPC ..................... 568/1, 17, 706; 562/7; 558/48, 558/72
See application file for complete search history.

(56) References Cited

PUBLICATIONS

Corbet et al., "Selected Patented Cross-Coupling Reaction Technologies". Chem. Rev., vol. 106, 2006, pp. 2651-2710.
Cyranski et al., "Separation of the Energetic and Geometric Contribution to Aromaticity. Part X. The Case of Benzene Rings in Fused Polycyclic Benzenoid Hydrocarbons". Tetrahedron, vol. 54, 1998, pp. 14919-14924.
Dallaire et al., "Nickel-Catalyzed Coupling of Aryl O-Carbamates With Grignard Reagents: 2,7-Dimethylnaphthalene". Organic Synthesis, Coll. vol. 10, 2004, p. 332; vol. 78, 2002, p. 42.
Dankwardt, "Nickel-Catalyzed Cross-Coupling of Aryl Grignard Reagents with Aromatic Alkyl Ethers: An Efficient Synthesis of Unsymmetrical Biaryls". Angew. Chem. Int. Ed., vol. 43, 2004, pp. 2428-2432.
Dankwardt, "Transition metal catalyzed cross-coupling of aryl Grignard reagents with aryl fluorides via Pd-or Ni-activation of the C-F bond: an efficient synthesis of unsymmetrical biaryls—application of microwave technology in ligand and catalyst screening". Journal of Organometallic Chemistry, vol. 690, 2005, pp. 932-938.
Doucet, "Suzuki-Miyaura Cross-Coupling Reactions of Alkyboronic Acid Derivatives or Alkyltrifluoroborates with Aryl, Alkenyl or Alkyl Halides and Triflates". Eur. J. Org. Chem., 2008, pp. 2013-2030.
Espinet et al., "The Mechanisms of the Still Reaction". Angew. Chem. Int. Ed., vol. 43, 2004, 4704-4734.
Goosen et al., "C(aryl)-O Activation of Aryl Carboxylates in Nickel-Catalyzed Biaryl Syntheses". Angew. Chem. Int. Ed., vol. 48, 2009, pp. 3569-3571.
Guan et al., "Methylation of arenes via Ni-catalyzed aryl C-O/F activation". Chem. Commun., 2008, pp. 1437-1439.
Guan et al., "Biaryl Construction via Ni-Catalyzed C-O Activation of Phenolic Carboxylates". J. Am. Chem. Soc., vol. 130, 2008, pp. 14468-14470.
Hassan et al., "Aryl-Aryl Bond Formation One Century after the Discovery of the Ullmann Reaction". Chem. Rev., vol. 102, 2002, pp. 1359-1469.
Lahti, "Localization of Aromaticity in Fused-Ring Cycloarene Systems: Prediction by an Effective Molecular Mechanics Model". Journal of Organic Chemistry, vol. 53, 1988, pp. 4590-4593.
Lipshutz et al., "Biaryls via Suzuki Cross-Coupling Catalyzed by Nickel on Charcoal". Tetrahedron, vol. 56, 2000, pp. 2139-2144.
Littke et al., "Palladium-Catalyzed Coupling Reactions of Aryl Chlorides". Angew. Chem. Int. Ed., vol. 42, 2002, pp. 4176-4211.
Macklin et al., "Directed Ortho Metalation Methodology. The N,N-Dialkyl Aryl O-Sulfamate as a New Directed Metalation Group and Cross-Coupling Partner for Grignard Reagents". Organic Letters, vol. 7, No. 13, 2005, pp. 2519-2522.
Miyaura et al., "Palladium-Catalyzed Cross-Coupling Reactions of Organoboron Compounds". Chem. Rev., vol. 95, 1995, 2457-2483.
Molander et al., "Development of the Suzuki-Miyaura Cross-Coupling Reaction: Use of Air-Stable Potassium Alkynyltrifluoroborates in Aryl Alkynylations". Journal of Organic Chemistry, vol. 67, 2002, pp. 8416-8423.
Munday et al., "Palladium-Catalyzed Carbonylation of Aryl Tosylates and Mesylates". J. Am. Chem. Soc., vol. 130, 2008, pp. 2754-2755.
Negishi et al., "Selective Carbon-Carbon Bond Formation via Transition Metal Catalysis. A Highly Selective Synthesis of Unsymmetrical Biaryls and Diarylmethanes by the Nickel-or Palladium-Catalyzed Reaction of Aryl-and Benzylzinc Derivatives with Aryl Halides". Journal of Organic Chemistry, vol. 42, No. 10, 1977, pp. 1821-1823.
Negishi, "Palladium-or Nickel-Catalyzed Cross Coupling. A New Selective Method for Carbon-Carbon Bond Formation". Acc. Chem. Res., vol. 15, 1982, pp. 340-348.
Negishi, "Transition Metal-Catalyzed Organometallic Reactions that Have Revolutionized Organic Synthesis". Bull. Chem. Soc. Jpn., vol. 80, No. 2, 2007, pp. 233-257.
Percec et al., "NiCl2(dppe)-Catalyzed Cross-Coupling of Aryl Mesylates, Arenesulfonates, and Halides with Arylboronic Acids". Journal of Organic Chemistry, vol. 69, 2004, pp. 3447-3452.
Quadorf et al., "Cross-Coupling Reactions of Aryl Pivalates with Boronic Acids". J. Am. Chem. Soc., vol. 130, 2008, pp. 14422-14423.

(Continued)

*Primary Examiner* — Charanjit Aulakh
(74) *Attorney, Agent, or Firm* — Gates & Cooper LLP

(57) ABSTRACT

Embodiments of the invention provide methods and materials for chemical cross-coupling reactions that utilize unconventional phenol derivatives as cross-coupling partners. Embodiments of the invention can be used to synthesize a variety of useful organic compounds, for example the anti-inflammatory drug flurbiprofen.

16 Claims, 14 Drawing Sheets

(56) References Cited

PUBLICATIONS

Quasdorf et al., "Suzuki-Miyaura Coupling of Aryl Carbamates, Carbonates, and Sulfamates". J. Am. Chem. Soc., vol. 131, 2009, pp. 17748-17749.

Schaub et al., "Catalytic C-C Bond Formation Accomplished by Selective C-F Activation of Perfluorinated Arenes". J. Am. Chem. Soc., vol. 128, 2006, pp. 15964-15965.

Sengupta et al., "Ni(0)-Catalyzed Cross Coupling of Aryl O-Carbamates and Aryl Triflates with Grignard Reagents. Directed Ortho Metalation-Aligned Synthetic Methods for Polysubstituted Aromatics via a 1,2-Dipole Equivalent". Journal of Organic Chemistry, vol. 57, 1992, pp. 4066-4068.

Stille, "The Palladium-Catalyzed Cross-Coupling Reaction of Organotin Reagent with Organic Electrophiles". Angew. Chem. Int. Ed. Engl., vol. 25, 1986, pp. 508-524.

Suzuki, "Carbon-carbon bonding made easy". Chem. Commun., 2005, pp. 4759-4763.

Tamao et al., "Selective Carbon-Carbon Bond Formation by Cross-Coupling of Grignard Reagents with Organic Halides. Catalysis by Nickel-Phosphine Complexes". Journal of the American Society, vol. 94, No. 12., 1972, pp. 4374-4376.

Tang et al., "Room-Temperature Ni(0)-Catalyzed Cross-Coupling Reactions of Aryl Arenesulfonates with Arylboronic Acids". J. Am. Chem. Soc., vol. 126, 2004, pp. 3058-3059.

Tobisu et al., "Nickel-Catalyzed Cross-Coupling of Aryl Methyl Ethers with Aryl Boronic Esters". Angew. Chem. Int. Ed., vol. 47, 2008, pp. 4866-4869.

Tobisu et al., "Devising Boron Reagents for Orthogonal Functionalization through Suzuki-Miyaura Cross-Coupling". Angew. Chem. Int. Ed., vol. 48, 2009, pp. 3365-3568.

Wehn et al., "Exploring New Uses for C-H Amination: Ni-Catalyzed Cross-Coupling of Cyclic Sulfamates". Organic Letters, vol. 7, No. 21, 2005, pp. 4685-4688.

Wender et al., "Function-Oriented Synthesis, Step Economy, and Drug Design". Accounts of Chemical Research, vol. 41, No. 1, 2008, pp. 40-49.

Wenkert et al., "Nickel-Induced Coversion of Carbon-Oxygen into Carbon-Carbon Bonds. One-Step Transformations of Enol Ethers into Olefins and Aryl Ethers into Biaiyls". Journal of the American Chemical Society, vol. 101, No. 8, 1979, pp. 2246-2247.

Wenkert et al., "Transformation of Carbon-Oxygen into Carbon-Carbon Bonds Mediated by Low-Valent Nickel Species". Journal of Organic Chemistry, vol. 49, 1984, pp. 4894-4899.

Yoshikai et al., "Nickel-Catalyzed Cross-Coupling Reaction of Aryl Fluorides and Chlorides with Grignard Reagent under Nickel/Magnesium Bimetallic Cooperation". J. Am. Chem. Soc., vol. 127, 2005, pp. 17978-17979.

Yoshikai et al., "Hydroxyphosphine Ligand for Nickel-Catalyzed Cross-Coupling through Nickel/Magnesium Bimetallic Cooperation". J. Am. Chem. Soc., vol. 131, 2009, pp. 9590-9599.

Zhang et al., "Palladium-Catalyzed Suzuki-Miyaura Cross-Coupling of Aryl Tosylates with Potassium Aryltrifluoroborates". Journal of Organic Chemistry, vol. 72, 2007, pp. 9346-9349.

FIG. 2

Table 1. Cross-Coupling of Pivalate 1

Ar-OPiv (1) + ArB(OH)₂ (2a-f) → NiCl₂(PCy₃)₂ (5 mol%), K₃PO₄ (4.5 equiv), toluene (0.3 M), 24 h → Ar-naphthyl (3a-f)

| entry | ArB(OH)₂[a] | | temp (°C) | yield[b] |
|---|---|---|---|---|
| 1 | PhB(OH)₂ | 2a | 80 °C | 92% |
| 2 | Me-C₆H₄-B(OH)₂ | para 2b | 80 °C | 91% |
| 3 | | meta 2c | 80 °C | 99% |
| 4 | | ortho 2d | 130 °C | 58% |
| 5 | CF₃-C₆H₄-B(OH)₂ | 2e | 120 °C | 82% |
| 6 | OMe-C₆H₄-B(OH)₂ | 2f | 80 °C | 95% |
| 7 | | | 80 °C | 86%[c] |

[a] 2.5 equiv ArB(OH)₂ employed. [b] Isolated yields. [c] Prepared in one-pot from 1-naphthol; conditions: i) PivCl, K₃PO₄, toluene, 80 °C; ii) 2f, 80 °C

Table 2. Cross-Coupling of Aryl Pivalates with Phenylboronic Acid

Ar-OPiv (1) + PhB(OH)₂ (2a)[a] → NiCl₂(PCy₃)₂ (5 mol%), K₃PO₄, toluene (0.3 M), 24 h → Ar-Ph

| entry | Ar | temp (°C) | yield[b] |
|---|---|---|---|
| 1 | 2-naphthyl | 110 °C | 91% |
| 2 | 6-(MeO₂C)-2-naphthyl | 110 °C | 72% |
| 3 | 4-OMe-1-naphthyl | 110 °C | 80% |
| 4 | N-Me-carbazolyl | 110 °C | 82% |
| 5 | 5,6,7,8-tetrahydro-1-naphthyl | 80 °C | 79% |

[a] Entries 1–4: 4 equiv ArB(OH)₂; Entry 5: 2.5 equiv ArB(OH)₂. [b] Isolated yields.

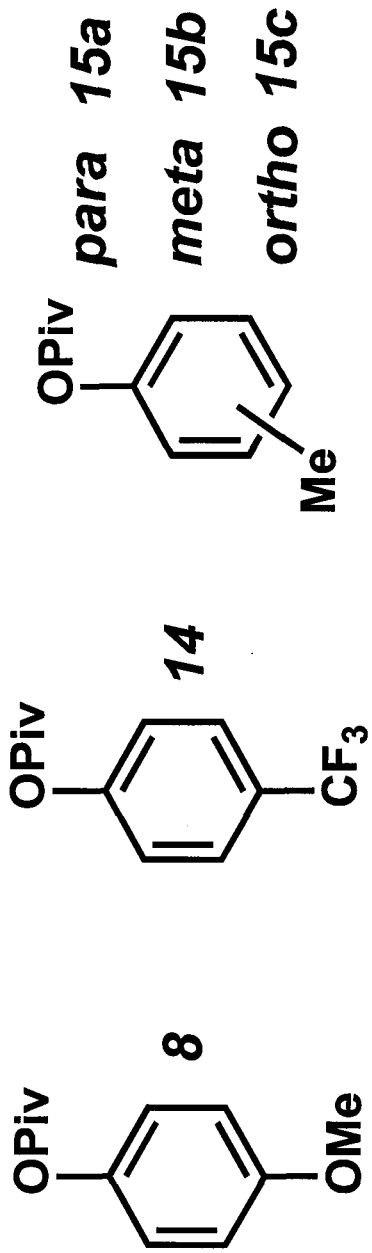

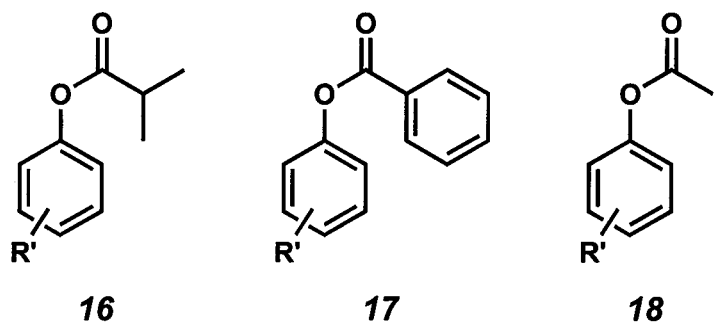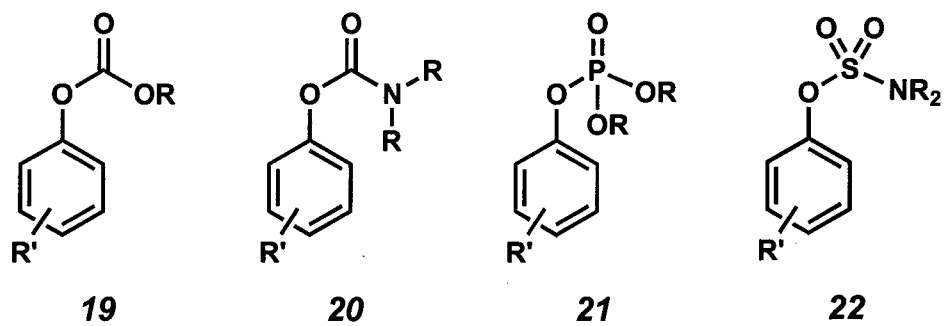
FIG. 3E

FIG 5D

| entry | R–OSO₂NMe₂ | (HO)₂B–Ar | product | yield[b] |
|---|---|---|---|---|
| 1 | 1-naphthyl-OSO₂NMe₂ | 2b | 1-(4-methoxyphenyl)naphthalene | 95% |
| 2 | 6-(MeO₂C)-2-naphthyl-OSO₂NMe₂ | 2a | 6-(MeO₂C)-2-phenylnaphthalene | 72% |
| 3 | 4-MeO-1-naphthyl-OSO₂NMe₂ | 2a | 4-MeO-1-phenylnaphthalene | 92% |
| 4 | Ph-OSO₂NMe₂ | 2b | 4-methoxybiphenyl | 87% |
| 5 | 4-Me-C₆H₄-OSO₂NMe₂ | 2b | 4-Me-4'-OMe-biphenyl | 89% |
| 6 | 3-Me-C₆H₄-OSO₂NMe₂ | 2b | 3-Me-4'-OMe-biphenyl | 91% |
| 7 | 2-Me-C₆H₄-OSO₂NMe₂ | 2b | 2-Me-4'-OMe-biphenyl | 92% |
| 8 | 2,6-Me₂-C₆H₃-OSO₂NMe₂ | 2b | 2,6-Me₂-4'-OMe-biphenyl | 63% |
| 9 | 4-F₃C-C₆H₄-OSO₂NMe₂ | 2a | 4-F₃C-biphenyl | 81% |
| 10 | 4-MeO-C₆H₄-OSO₂NMe₂ | 2a | 4-MeO-biphenyl | 80% |
| 11 | 4-Me₂N-C₆H₄-OSO₂NMe₂ | 2a | 4-Me₂N-biphenyl | 76% |
| 12 | 1-Me-indol-5-yl-OSO₂NMe₂ | 2a | 1-Me-5-phenylindole | 75% |
| 13 | 3-oxocyclohex-1-en-1-yl-OSO₂NMe₂ | 2a | 3-phenylcyclohex-2-enone | 75% |
| 14[c] | R = TMS | 2b | X = OMe | 92% |
| 15 | R = Ph | 2b | X = OMe | 93% |
| 16 | R = OMe (2-R-C₆H₄-OSO₂NMe₂) | 2a | X = H | 90% |
| 17[c] | R = C(O)tBu | 2a | X = H | 85% |

# CROSS-COUPLING OF PHENOLIC DERIVATIVES

CROSS REFERENCE TO RELATED APPLICATIONS

This application claims the benefit of U.S. provisional patent application No. 61/245,752, filed Sep. 25, 2009, the entire contents of which are incorporated herein by reference.

STATEMENT OF GOVERNMENT SUPPORT

This invention was made with Governmental support of Grant No. GMO79922 awarded by the National Institutes of Health. The United States Government has certain rights in the invention.

BACKGROUND OF THE INVENTION

1. Field of the Invention

The present invention relates to methods and materials for the synthesis of organic compounds.

2. Description of Related Art

Methodologies involving the synthesis of organic molecules play an important role in many technical fields. Materials science, agriculture, biology, and medicine, rely on organic compounds produced by synthetic methods for their ongoing successes and future progress. Consequently, in the past century artisans have devoted significant efforts to the development of new methodologies for the synthesis of various organic compounds. The large number of synthetic methodologies known in the art as a result of these endeavors allows artisans to construct molecules of great complexity. As complex organic molecules become more and more important in a number of scientific disciplines, the ability to prepare key synthetic entities in both a practical and economical fashion becomes increasingly more valuable (see, e.g. Wender et al., Acc. Chem. Res. 2008, 41, 40-49).

Of the many synthetic methods used to generate organic compounds, transition metal-catalyzed cross-coupling reactions are known as one of the most effective means of constructing carbon-carbon (C—C) and carbon-heteroatom (C—X) bonds (see, e.g. Negishi et al., Acc. Chem. Res. 1982, 15, 340-348; Metal-Catalyzed Cross-Coupling Reactions; Diedrich, F., Meijere, A., Eds.; Wiley-VCH: Weinheim, 2004; Vol. 2.; Hassan et al., Chem. Rev. 2002, 102, 1359-1469; Topics in Current Chemistry; Miyaura, N., Ed.; Vol. 219; Springer-Verlag: New York, 2002; Corbet et al.,Rev. 2006, 106, 2651-2710; Negishi, Bull. Chem. Soc. Jpn. 2007, 80, 233-257). These bonds are commonly found in a variety of compounds, and, for example, are ubiquitous in drug substances. Illustrating this, eight of the top twenty best selling drug compounds in 2007 possessed either an aryl-aryl C—C bond or an aryl C—X bond. The combined 2007 sales for these compounds amounted to nearly twenty billion dollars (compounds including for example, Lipitor®, Singular®, Seroquel®, and Celebrex®).

While methodologies for the cross-coupling of aryl halides have improved significantly over the past decade, less progress has been made in methods for the coupling of the corresponding phenol derivatives. Because phenols are typically cheap and readily available, and further because oxygenation can be used to direct the installation of functional groups on an aromatic ring, practical methods that allow for the cross-coupling of phenol derivatives are extremely desirable. Although some methods for cross-coupling phenol derivatives exist, there is a need to improve existing methodology (see, e.g. the schematic shown in FIG. 1A). Of the known methods for phenol coupling, the most common involve formation and reaction of the corresponding aryl triflates (see, e.g. Negishi et al., Acc. Chem. Res. 1982, 15, 340-348; Metal-Catalyzed Cross-Coupling Reactions; Diedrich, F., Meijere, A., Eds.; Wiley-VCH: Weinheim, 2004; Vol. 2.; Hassan et al., Chem. Rev. 2002, 102, 1359-1469; Topics in Current Chemistry; Miyaura, N., Ed.; Vol. 219; Springer-Verlag: New York, 2002;Corbet et al., Rev. 2006, 106, 2651-2710; Negishi, Bull. Chem. Soc. Jpn. 2007, 80, 233-257). Unfortunately, aryl triflates species used in phenol coupling reactions are relatively costly. In addition, these compounds are susceptible to base-promoted hydrolysis (see, e.g. Molander et al., J. Org. Chem. 2002, 67, 8416-8423). Moreover, while aryl tosylates (-OTs) and mesylates (-OMs) have also been used as cross-coupling partners, these molecules do not appear to have general utilities (see, e.g. Tang et al., J. Am. Chem. Soc. 2004, 126, 3058-3059; Percec et al., J. Org. Chem. 2004, 69, 3447-3452; Zhang et al., J. Org. Chem. 2007, 72, 9346-9349; Munday et al., J. Am. Chem. Soc. 2008, 130, 2754-2755). Cross-coupling reactions of aryl methyl ethers (OMe), although largely limited to Kumada couplings using harsh Grignard reagents, are also known in the art (see, e.g. Wenkert et al., J. Am. Chem. Soc. 1979, 101, 2246-2247; Wenkert et al., J. Org. Chem. 1984, 49, 4894-4899; Dankwardt et al., Angew. Chem. Int. Ed. 2004, 43, 2428-2432; and Guan et al., Chem. Commun. 2008, 1437-1439). A recent report by Chatani and co-workers somewhat expands the scope of this cross-coupling to arylboronic acids, provided that the aryl ether cross-coupling partner is electron-deficient and preferably contained within a highly reactive fused aromatic ring system (see, e.g. Tobisu et al., Angew. Chem. Int. Ed. 2008, 47, 4866-4869). Despite some advances in this technology, general methodologies that provide efficient and cost-effective cross-coupling of phenol derivatives have yet to be realized.

SUMMARY OF THE INVENTION

The invention disclosed herein relates to chemical reactions for the synthesis of organic compounds, in particular those that utilize unconventional phenol derivatives as cross-coupling partners. Embodiments of the invention provide efficient and cost-effective cross-coupling reactions that can be used to synthesize a wide variety of cross-coupled compounds including, for example, the anti-inflammatory drug flurbiprofen. A general embodiment of the invention comprises a method for making a cross-coupled compound by combining together: an organoboron compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In such embodiments of the invention, the organoboron compound, the aryl alcohol derivative and the transition metal catalyst are combined so as to allow a cross-coupling reaction between the organoboron compound, the aryl alcohol derivative and the transition metal catalyst that results in the formation of the cross-coupled compound, typically in a yield of at least 25%. In certain embodiments of the invention, the cross-coupling reaction results in the formation of the cross-coupled compound in a yield of at least 50%.

A related embodiment of the invention is a method for performing a Suzuki-Miyaura cross-coupling reaction comprising combining together: an organoboron compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In this embodiment of the invention, the organoboron compound, the aryl alcohol derivative and the transition metal catalyst are combined so as to allow: oxidative addition of the transition metal catalyst and generation of a first organo-transition metal species; reaction between the first organo-transition metal species and the organoboron compound and generation of a second organo-transition metal species; and reductive elimination of the second organo-transition metal species, regeneration of the transition metal catalyst and generation of a cross-coupled compound, typically in a yield of at least 25%. In certain embodiments of the invention, the cross-coupling reaction results in the formation of the cross-coupled compound in a yield of at least 50%.

Yet another embodiment of the invention is a cross-coupled compound made by a process comprising combining together: an organoboron, organostannane, organozinc or organomagnesium compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In this embodiment, the organoboron, organostannane, organomagnesium or organozinc compound, the aryl alcohol derivative and the transition metal catalyst are combined so as to allow chemical reaction between the organoboron, organostannane, organomagnesium or organozinc compound, the aryl alcohol derivative and the transition metal catalyst, wherein the reaction results in the formation of the cross-coupled compound, typically in a yield of at least 25%. In certain embodiments of the invention, the cross-coupling reaction results in the formation of the cross-coupled compound in a yield of at least 50%.

Embodiments of the invention can employ a variety of methods and materials in order to, for example, control aspects of the cross-coupling reactions. In typical embodiments of the invention, the organoboron compound comprises an organoboronic acid, a diorganoborinic acid, a organoboronate ester, an organoboroxine, a organotrialkoxyborate, an organotrifluoroborate, an organotrihydroxyborate, a tetraorganoborate, a triorganoborane, an alkylborane or a tetrafluoroborate compound. In some embodiments of the invention, aryl alcohol derivative comprises a heteroatom. In typical embodiments of the invention, the transition metallic catalyst comprises nickel. In certain embodiments, the transition metal catalyst comprises an air stable Ni(II) precatalyst complex prior to its combination with the organoboron compound and the aryl alcohol derivative. In embodiments of the invention, the transition metal catalyst can be regenerated simultaneously with formation of the cross-coupled compound. In certain embodiments of the invention, the cross-coupled compound is formed from a one-pot synthesis and/or the cross-coupling reaction is not performed in a glovebox.

Certain embodiments of the methods for making cross-coupled compounds include further steps to modify and/or purify these compounds. For example, in certain embodiments of the invention, the cross-coupled compound generated by an embodiment of the invention is an intermediate in the synthesis of a target compound (e.g. flurbiprofen). In such embodiments, the further steps can include, for example, performing a base mediated hydrolysis on the cross-coupled compound. Alternatively, the further steps can include, for example, performing an acid mediated hydrolysis on the cross-coupled compound. Embodiments of the invention can also include at least one purification step, for example a purification step comprising the filtration, extraction, distillation or precipitation of one or more compounds generated by the cross-coupling reaction.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 2 provides tables showing the cross-coupling of various arylboronic acid compounds. Table 1 shows that a variety of arylboronic acids particulate as partners in the Ni-catalyzed cross-coupling of naphthyl pivalate 1. Substitution is tolerated at the p, m, and o-positions as demonstrated by the coupling of tolyl substrates 2b-d (entries 2-4 in Table 1 of FIG. 2), respectively, although the o-substituted substrate (entry 4) requires elevated temperatures for modest success. Similarly, electron-deficient boronic acid 2e cross-couples at 120° C. to afford 3e in 82% yield (entry 5). Electron-rich substrate, 2f, bearing a p-methoxy substituent was also a competent cross-coupling partner (entry 6). Table 1 further shows results from a powerful one-pot process to access biaryl adducts directly from 1-naphthol (entry 7). $^a$2.5 equiv ArB(OH)$_2$ employed. $^b$ Isolated yields. $^c$ prepared in one-pot from 1-naphthol; conditions: i) PivCl, K$_3$PO$_4$, toluene, 80° C] ii) 2f, 80° C.

Figure 1A:
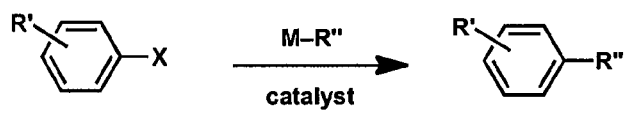
FIG. 1A provides a schematic showing phenol derivative compounds used in cross-coupling reactions known in the art in comparison to aspects the invention disclosed herein.
Figure 1B:
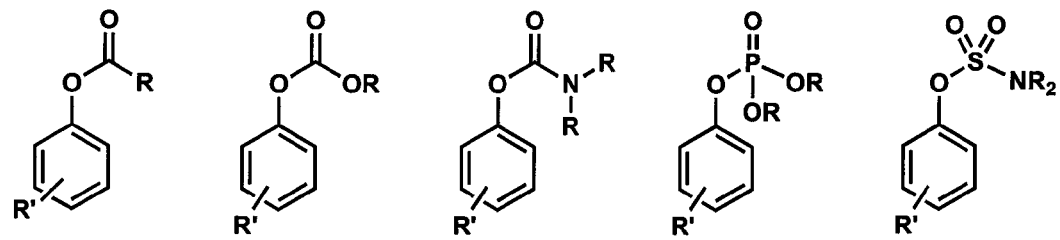
FIG. 1B provides a schematic showing unconventional phenol derivatives useful in embodiments of the invention disclosed herein.

In Table 2, the scope of embodiments of the invention was then demonstrated by varying the aryl pivalate component. As shown in Table 2, cross-coupling of phenylboronic acid (2a) with the naphthyl pivalate substrate derived from 2-naphthol proceeded in 91% yield. In addition, the reaction proved tolerant of an electron-withdrawing group (—CO$_2$Me, entry 2) and an electron-donating group (—OMe, entry 3) on the naphthyl ring. The Suzuki-Miyaura coupling of a substrate derived from N-Me-2-hydroxycarbazole proceeded in 82% yield (entry 4). Furthermore, a vinyl pivalate derived from tetralone was found to be a suitable cross-coupling partner (entry 5). $^a$Entries 1S4: 4 equiv ArB(OH)$_2$; Entry 5: 2.5 equiv ArB(OH)$_2$. $^b$ Isolated yields.

Figure 3A:
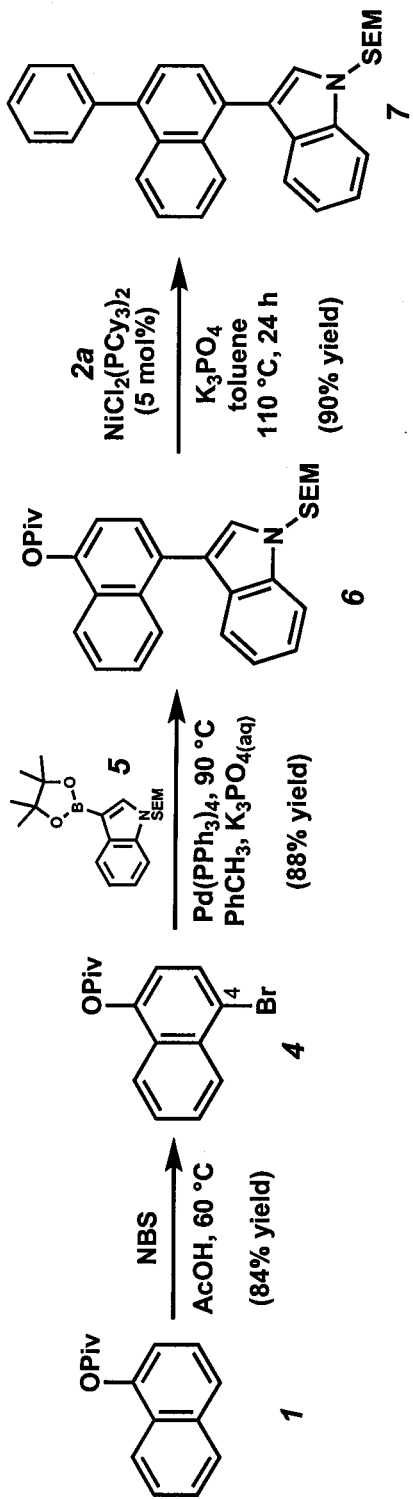
Figure 3B:
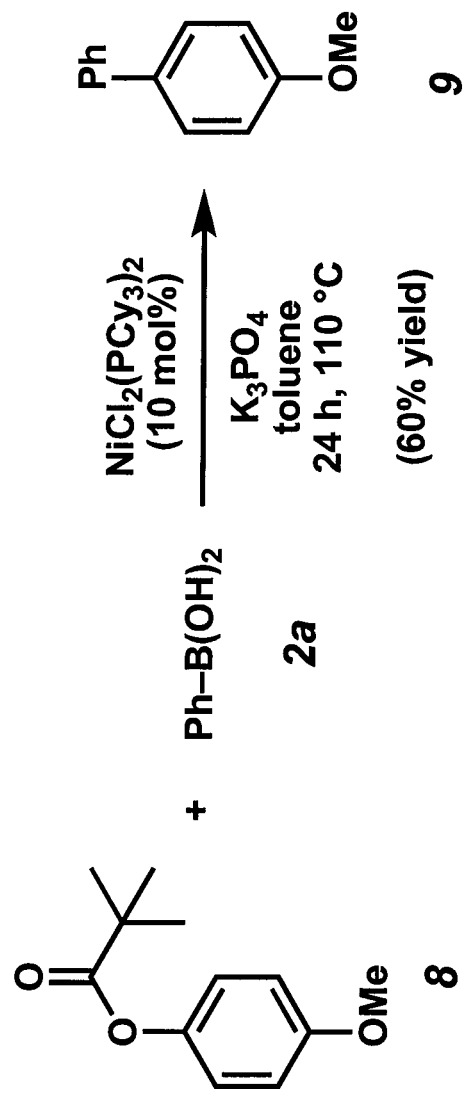
Figure 3C:
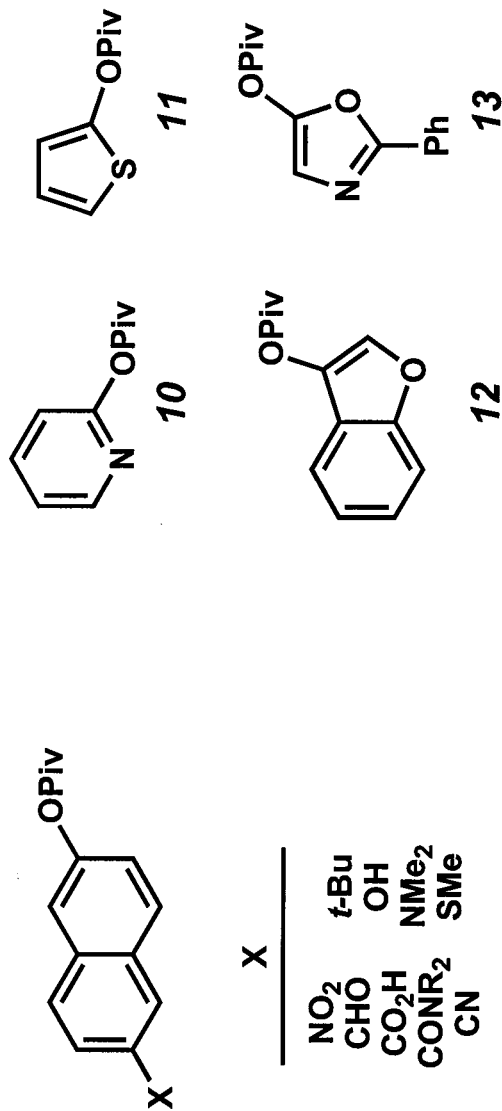

FIG. 3A provides a schematic showing aryl pivalates as a directing group and orthogonal cross-coupling reactions. A key advantage to the use of pivalates is their ability to direct the installation of functional groups onto an aromatic ring. A demonstration of this feature is highlighted in Scheme 2, where naphthyl pivalate 1 was selectively brominated at C4 to afford bromopivalate 4 in 84% yield. FIG. 3B provides a schematic showing Suzuki-Miyaura Coupling of Non-Fused Aryl Pivalates. As shown in FIG. 3B, in a unoptimized process, coupling of electron-rich pivalate 8 with phenylboronic acid (2a) afforded biaryl adduct 9 in 60% isolated yield, with the remaining mass correlating to p-methoxyphenol. FIG. 3C provides a schematic showing an assortment of 2,6-disubstituted naphthyl pivalates bearing either an electron-donating or an electron-withdrawing groups and additional heterocyclic pivalates. FIG. 3D provides a schematic showing non-fused aryl substrates. FIG. 3E provides a schematic showing alternatives to pivalate esters such as isobutyrates 16, benzoates 17, and acetates 18.

Figure 4:
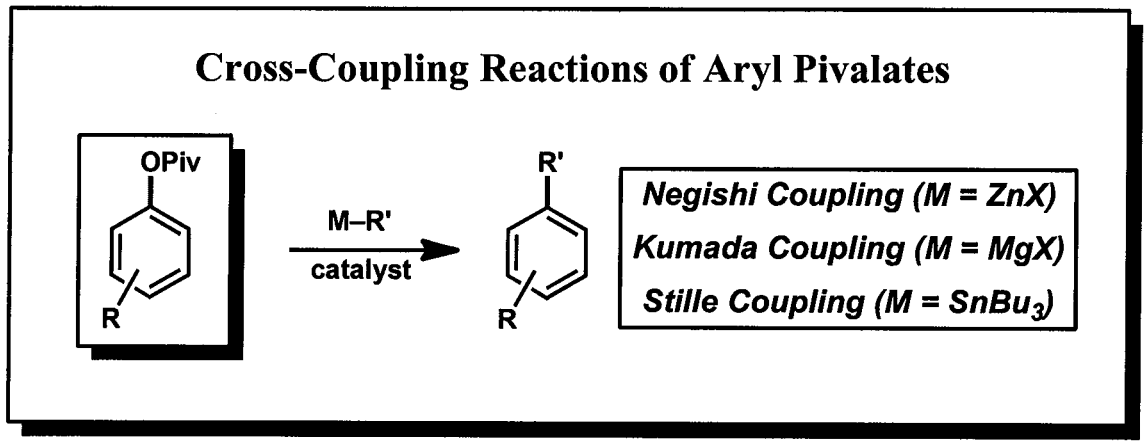

FIG. 4 provides a schematic showing various cross-coupling reactions of aryl pivalates.

Figure 5A:
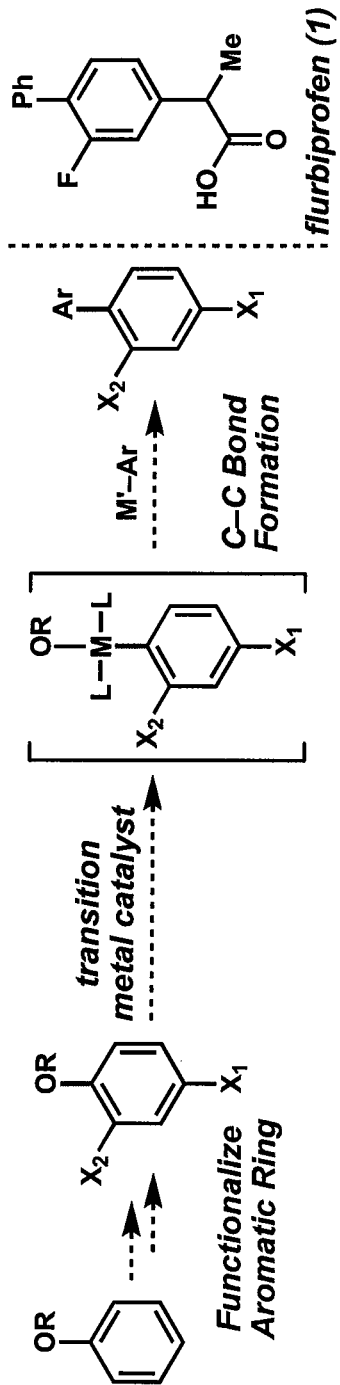
Figure 5B:
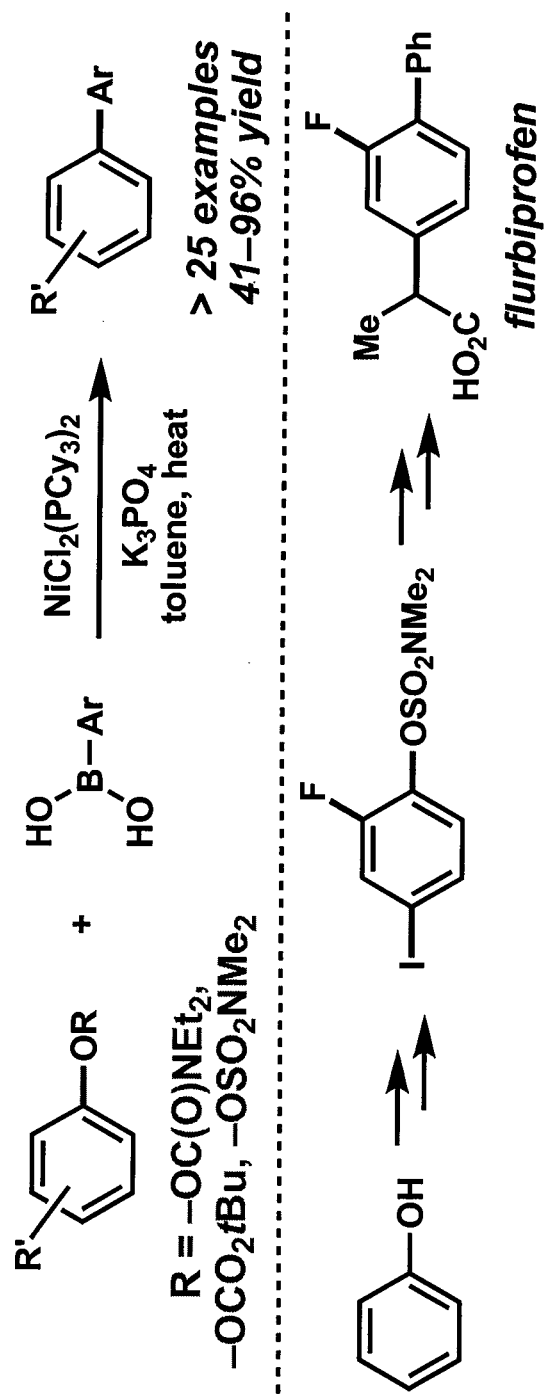
Figure 5C:
Figure 5E:
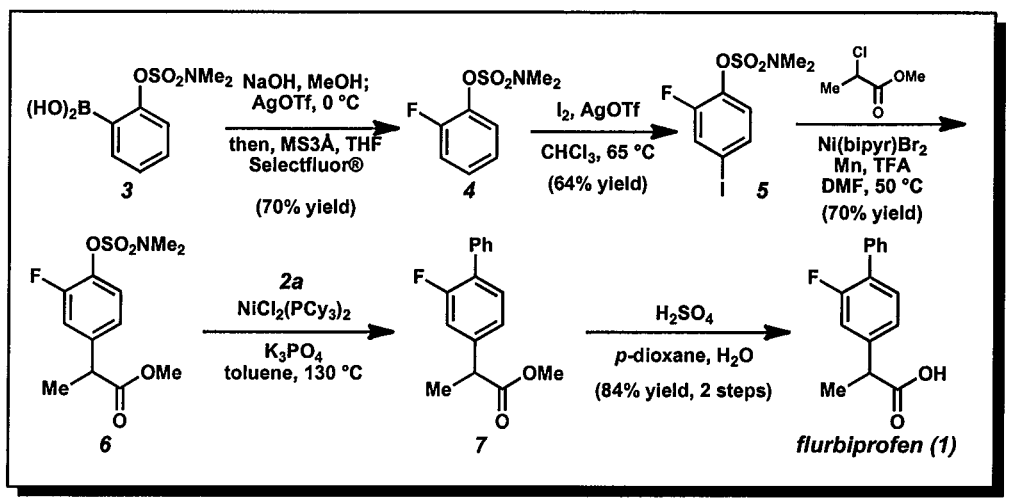

FIG. 5A provides a schematic showing an approach to generating polysubstituted aromatics such as flurbiprofen. FIG. 5B also provides a schematic showing an approach to generating polysubstituted aromatics such as flurbiprofen. FIG. 5C provides a table showing the cross-coupling of various aryl carbamates and carbonates with arylboronic acids. FIG. 5D provides a table showing the cross-coupling of various aryl sulfamates. FIG. 5E also provides a schematic showing the synthesis of flurbiprofen using orthogonal cross-couplings.

DETAILED DESCRIPTION OF THE EMBODIMENTS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. All numbers recited in the specification and associated claims that refer to values that can be numerically characterized can be modified by the term "about".

As is known in the art, "coupling reactions" refers to a range of reactions in organometallic chemistry where two hydrocarbon fragments are coupled with the aid of a metal containing catalyst. Coupling reactions include "cross-coupling reactions" in which two different molecules react to form one new molecule, for example the nickel chloride catalyzed reaction of an aryl magnesium halide with an aryl halide to form a biaryl. As used herein, a "cross-coupled compound" is a compound formed by a cross-coupling reaction. As is known in the art, in chemistry a "derivative" (e.g. a "phenol derivative") is a compound that is derived from a similar compound or a compound that can be imagined to arise from another compound, if one atom is replaced with another atom or group of atoms. As discussed in detail below, embodiments of this invention relate to methods and materials for making organic compounds through the chemical coupling reactions disclosed herein, for example those that utilize unconventional phenol derivatives as cross-coupling partners.

While various attempts to achieve the cross-coupling of acylated phenols have been previously described in the art, all have been met with little success (see, e.g. Guan et al., *Chem. Commun.* 2008, 1437-1439; and Tobisu et al., *Angew. Chem. Int. Ed.* 2008, 47, 4866-4869). In this context, embodiments of the invention disclosed herein provide cost-effective methods for introducing C—X or C—C bonds into organic compounds, for example organic compounds that have uses in medical fields (e.g. Lipitor®, Singular®, Seroquel®, and Celebrex®). In addition, embodiments of the invention allows for the one-pot conversion of phenols into cross-coupled products, a desirable practice which is not possible using previously described methodologies for making cross-coupled compounds. Moreover, the ability to cross-couple such substrates following the methods disclosed herein is beneficial because acylated phenols are exceedingly simple to prepare, are amongst the most affordable phenol derivatives available, are stable to a variety of reaction conditions, and are able to direct the installation of other functional groups onto an aromatic ring (see, e.g. FIG. 1A, as well as Greene, T. W.; Wuts, P. G. M. *Greene's Protective Groups in Organic Synthesis*; 4th ed.; John Wiley & Sons, Inc.: New Jersey, 2007; Snieckus et al., *Chem. Rev.* 1990, 90, 879-933; and Smith, M. B.; March, J. *March's Advanced Organic Chemistry*; 6th ed.; John Wiley & Sons, Inc.: New Jersey, 2007; p 668).

One illustrative embodiment of the invention comprises a method for making a cross-coupled compound by combining together: an organoboron compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In such embodiments of the invention, the organoboron compound, the aryl alcohol derivative and the transition metal catalyst are combined so as to allow a cross-coupling reaction between the organoboron compound, the aryl alcohol derivative and the transition metal catalyst that results in the formation of the cross-coupled compound.

As noted above, the terminology used herein is intended to have the meanings commonly understood by those of skill in the art to which this invention pertains. For example, as is known in the art, "organoboron compounds" are chemical compounds that are organic derivatives of BH3, for example alkyl boranes (see, e.g. *The Roles of Boron and Silicon*, Susan E. Thomas; Oxford Chemistry Primers No.1; 1991; and*Organometallics* Christoph Elschenbroich 3rd Ed. 2006 ISBN 3-527-29390-6-Wiley-VCH, Weinheim). Organoboron compounds are important reagents in organic chemistry enabling many chemical transformations, for example hydroboration. As is known in the art, a "transition metal" is an element whose atom has an incomplete d sub-shell, or which can give rise to cations with an incomplete d sub-shell.

As used herein, the term "alkyl" refers to a branched or unbranched saturated hydrocarbon group typically although not necessarily containing about 1-24 carbon atoms, unless indicated otherwise. Exemplary alkyl groups include methyl, ethyl, n-propyl, isopropyl, n-butyl, isobutyl, t-butyl, n-amyl, isoamyl, n-hexyl, n-heptyl, n-octyl, n-decyl, hexyloctyl, tetradecyl, hexadecyl, eicosyl, tetracosyl, and the like, as well as cycloalkyl groups such as cyclopropyl, cyclobutyl, cyclopentyl, cyclohexyl, cycloheptyl, cyclooctyl and the like. Generally, although again not necessarily, alkyl groups herein contain about 1-12 carbon atoms. The term "lower alkyl" refers to an alkyl group of 1-6 carbon atoms, e.g. 1-4 carbon atoms. The alkyl group is optionally substituted at one or more positions. Exemplary substituents include but are not limited to hydroxyl, cyano, alkoxy, =O, =S, —NO$_2$, halo, heteroalkyl, amine, thioether, —SH, and aryl. Accordingly, if not otherwise indicated, the terms "alkyl" includes branched, unbranched, unsubstituted, and substituted alkyl groups. The term "cycloalkyl" refers to a cyclic alkyl, as defined above, and is typically a stable 3- to 7 membered monocyclic or 7- to 10-membered polycyclic ring which is saturated or partially unsaturated (e. g., containing one or more double bonds). Similarly, the term "cycloheteroalkyl" is intended to mean a cyclic alkyl group, as defined above, that contains one or more heteroatoms, and is typically a stable 3- to 7 membered monocyclic or 7- to 10-membered polycyclic ring which is saturated or partially unsaturated and contains 1 4 heteroatoms (N, O, S, P or Si). As with alkyl, the terms "cycloalkyl" and "cycloheteroalkyl" are intended to include both unsubstituted and substituted groups. The substitutions can be on a carbon or a heteroatom if the resulting compound is stable. For example, any amino group contained within the heterocycloalkyl group can be a primary, secondary or tertiary amine, as long as the structure is stable. As used herein, the term "alkene" refers to unsaturated hydrocarbons having at least one double bond between two carbon atoms, and the term "alkenyl" refers to a group derived from an alkene.

As used herein, the term "aryl" is intended to mean an aromatic substituent containing a single aromatic ring (e.g., phenyl) or multiple aromatic rings that are fused together (e.g., naphthyl or biphenyl), directly linked, or indirectly linked (such that the different aromatic rings are bound to a common group such as a methylene or ethylene moiety). Typically, the aryl group comprises from 5 14 carbon atoms. Illustrative aryl groups contain one aromatic ring or two fused or linked aromatic rings, e.g., phenyl, naphthyl, biphenyl, diphenylether, diphenylamine, benzophenone, and the like. The aryl moiety may be independently substituted with one or more substituent groups, typically 1 3 substituents, including =O, —OH, —COOH, —CH$_2$—SO$_2$-phenyl, —C$_{1-6alkyl}$, —O—C$_{1-6alkyl}$, —C(O)—C$_{1-4alkyl}$, —(CH$_2$)$_{0-2}$—C(O)—O—C$_{1-4alkyl}$, cycloalkyl, —C$_{1-6alkoxy}$, halo, nitro, amino, alkylamino, dialkylamino, —C(O)—N(C$_{1-4alkyl}$)$_2$, —NH—C(O)—C$_{1-4alkyl}$, —C(O)—NH$_2$, —SO$_2$—NH$_2$, trifluoromethyl, cyano, aryl, benzyl, —O-aryl and —S-aryl. Thus, the term "aryl" includes unsubstituted and substituted aryl groups. The term "heteroaryl" refer to aryl, as defined above, in which at least one carbon atom, typically 1-3 carbon atoms, is replaced with a heteroatom N, O, S, P or Si). The heteroaryl can have the heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like). As with aryl, the term "heteroaryl" is intended to include both unsubstituted and substituted heteroaryl groups. The substitutions can be on a carbon or a heteroatom if the resulting compound is stable. For example, any amino group contained within the heteroaryl group can be a primary, secondary or tertiary amine, as long as the structure is stable.

While attempts to achieve the cross-coupling of acylated phenols have been described, all have been met with little success (see, e.g. Guan et al., Chem. Commun. 2008, 1437-1439; and Tobisu et al., Angew. Chem. Int. Ed. 2008, 47, 4866-4869). In contrast, as shown by the variety of illustrative embodiments of the invention disclosed in Examples 1 and 2 below, the methodologies disclosed herein successfully achieve the cross-coupling of acylated phenols to produce cross-coupled products in highly efficient yields, thereby overcoming problems observed in this art. Typically, a method for producing a cross-coupled compound as disclosed herein produces a cross-coupled compound in a yield of at least 25%. In certain embodiments of the invention, the cross-coupling reaction results in the formation of the cross-coupled compound in a yield of at least 30%, 40%, 50%, 60%, 70%, 80%, 90% or higher. As is known in the art, in chemistry, "yield", also referred to as chemical yield and reaction yield, is the amount of product obtained in a chemical reaction (see, e.g. Vogel, A. I., Tatchell, A. R., Furnis, B. S., Hannaford, A. J. and P. W. G. Smith. Vogel's Textbook of Practical Organic Chemistry, 5th Edition. Prentice Hall, 1996). The absolute yield can be given as the weight in grams or in moles (molar yield). The fractional yield, relative yield, or percentage yield, which serve to measure the effectiveness of a synthetic procedure, can be calculated by dividing the amount of the obtained product in moles by the theoretical yield in moles. To obtain the percentage yield, one can multiply the fractional yield by 100 (e.g., 0.673=67.3%). In one exemplary method for calculating yields, one can start with x moles (a defined amount) of a pivalate (or a sulfamate, etc.), with the consequential expectation of getting x moles of cross-coupled product following the cross-coupling reaction. Following the cross-coupling reaction, the pure product can be isolated and its weight determined. Using this determined weight, one can then convert to moles of cross-coupled produced, and then use this value to calculate yield. In such reactions, the amounts of the individual reactants can be manipulated to control, for example, stoichiometric parameters in these processes. For example, in such reactions one can use a boronic acid in excess, or alternatively, as a limiting reagent.

Another embodiment of the invention is a cross-coupled compound made by a process comprising combining together: an organoboron, organostannane, organomagnesium or organozinc compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In this embodiment, the organoboron, organostannane, organomagnesium or organozinc compound, the aryl alcohol derivative and the transition metal catalyst are combined so as to allow chemical reaction between the organoboron, organostannane, organomagnesium or organozinc compound, the aryl alcohol derivative and the transition metal catalyst, wherein the reaction results in the formation of the cross-coupled compound, typically in a yield of at least 25%. In certain embodiments of the invention, the cross-coupling reaction results in the formation of the cross-coupled compound in a yield of at least 50%.

Without being bound by a specific scientific mechanism or principle of action, embodiments of invention are characterized as "Suzuki-Miyaura coupling reactions" because the cross-coupling reactions disclosed herein are consistent with the descriptions of such reactions in this art. However, aryl pivalates are known to participate in cross-coupling reactions other than Suzuki-Miyaura couplings (see, e.g. those noted in FIG. 4). Related C—C bond forming processes, such as Negishi, Kumada, and Stifle couplings are contemplated in embodiments of the invention (see, e.g. Negishi et al., J. Org. Chem. 1977, 42, 1821-1823; Tamao et al., J. Am. Chem. Soc. 1972, 94, 4374-4376; Wender et al., Acc. Chem. Res. 2008, 41, 40-49; and Stille, J. K. Angew. Chem. Int. Ed. 1986, 25, 508-524; and Espinet et al., *Angew. Chem. Int. Ed.* 2004, 43, 4704-4734). Of these processes, the Stifle reaction holds particular promise, because it is possible that pivalate functional group on compounds used in embodiments of the invention may not be stable to Grignard and organozinc reagents needed for Kumada and Negishi couplings, respectively.

Another embodiment of the invention is a method for performing a Suzuki-Miyaura cross-coupling reaction comprising combining together: an organoboron compound; an aryl alcohol derivative, wherein the aryl alcohol derivative comprises an acylated aryl alcohol compound, an aryl carbamate compound, an aryl carbonate compound, an aryl sulfamate compound, or an aryl phosphate compound; and a transition metal catalyst, wherein the transition metallic catalyst comprises nickel or palladium. In this embodiment of the invention, the organoboron compound, the aryl alcohol derivative and the transition metal catalyst are combined so as to allow: oxidative addition of the transition metal catalyst and generation of a first organo-transition metal species; reaction between the first organo-transition metal species and the organoboron compound and generation of a second organo-transition metal species; and reductive elimination of the second organo-transition metal species, regeneration of the transition metal catalyst and generation of a cross-coupled compound, typically in a yield of at least 25%. In certain embodiments of the invention, the cross-coupling reaction results in the formation of the cross-coupled compound in a yield of at least 50%.

Embodiments of the invention can employ a variety of methods and materials in order to, for example, control aspects of the cross-coupling reactions. In typical embodiments of the invention, the organoboron compound comprises an organoboronic acid, a diorganoborinic acid, a organoboronate ester, an organoboroxine, a organotrialkoxyborate, an organotrifluoroborate, an organotrihydroxyborate, a tetraorganoborate, a triorganoborane, an alkylborane or a tetrafluoroborate compound. In some embodiments of the invention, aryl alcohol derivative comprises a heteroatom. As is known in the art, a "heteroatom" is: any atom in a heterocyclic ring (or other structure normally built of carbon atoms) that is not a carbon atom. Typical heteroatoms include nitrogen, oxygen, sulfur, phosphorus, boron, chlorine, bromine, or iodine.

In typical embodiments of the invention, the transition metallic catalyst comprises nickel. Optionally, the transition metallic catalyst comprises $NiCl_2(PCy_3)_2$, which is commercially available from Strem Chemicals Inc. (catalog #28-0091). As is known in the art, metallic catalysts comprise ligands (e.g. tricyclohexylphosphine as used in the illustrative embodiments of the invention that are disclosed herein). Those of skill in the art will understand that other ligand scaffolds such as phosphines, n-heterocyclic carbenes, amines, and the like can be used in embodiments of the invention. As is known in this art, often the active catalyst in a reaction is not the same as the initial catalyst introduced into the reaction (e.g. in situations where an initial catalyst is exposed to one or more reagents and/or reaction conditions in order to form the active catalyst). In certain embodiments, the transition metal catalyst comprises an air stable Ni(II) precatalyst complex prior to its combination with the organoboron compound and the aryl alcohol derivative. In embodiments of the invention, the transition metal catalyst can be regenerated simultaneously with formation of the cross-coupled compound.

Embodiments of the invention utilize a variety of reaction parameters. For example, reactions can be carried out at a range of temperatures (e.g. from 20° C. to 200° C.). Typically however, the reactions disclosed herein are keep at a temperature ranging from 80° C. to 130° C. Similarly, reactions can be carried out in the presence of a variety of organic solvents such as toluene, xylenes, dioxane, dimethoxyethane, benzene, tetrahydrofuran, dimethylformamide, dimethylacetamide, N-methylpyrrolidinone (and combinations of such solvents). In some embodiments of the invention, the cross-coupled compound is formed from a cross-coupling reaction that is performed in a glovebox. In other embodiments of the invention, the cross-coupled compound is formed from a cross-coupling reaction that is not performed in a glovebox. In some embodiments of the invention, the cross-coupled compound is formed from a one-pot synthesis. As is known in the art, a "one-pot synthesis" is a strategy to improve the efficiency of a chemical reaction whereby a reactant is subjected to successive chemical reactions in just one reactor. This is much desired by artisans in this technology because avoiding a lengthy separation process and purification of the intermediate chemical compounds saves time and resources while increasing chemical yield. In some embodiments of the invention where the cross-coupled compound is formed from a one-pot synthesis, the reactants can be premade and added into the reaction vessel. In other embodiments of the invention where the cross-coupled compound is formed from a one-pot synthesis, the reactants can be themselves synthesized in the reaction vessel in which the cross-coupled compound is subsequently formed.

Certain embodiments of the methods for making cross-coupled compounds include additional steps to further modify and/or purify these compounds. For example, in certain embodiments of the invention, the cross-coupled compound generated by an embodiment of the invention is an intermediate in the synthesis of a target compound such as flurbiprofen. In such embodiments, the further steps can include, for example, performing a base mediated hydrolysis on the cross-coupled compound. Alternatively, the further steps can include, for example, performing an acid mediated hydrolysis on the cross-coupled compound. Embodiments of the invention can also include at least one purification step, for example a purification step comprising the filtration, extraction, distillation or precipitation of one or more compounds generated by the cross-coupling reaction.

The Examples below provide a number of illustrative embodiments of the invention. In these studies, Suzuki-Miyaura couplings were chosen as a focus, mainly because of the numerous advantages of using boronic acids: their low toxicity, wide availability, stability to water and air, and high functional group tolerance. As part of this, several potential challenges were addressed at the outset. First, the acylated phenol substrates can be prone to hydrolysis under typical Suzuki-Miyaura conditions involving aqueous bases. Thus, robust pivalate esters (Ar—OC(O)CMe$_3$) (see, e.g. Greene, T. W.; Wuts, P. G. M. *Greene's Protective Groups in Organic Synthesis*; 4th ed.; John Wiley & Sons, Inc.: New Jersey, 2007) were selected as the acylated phenol derivatives of first choice. In addition, it is postulated that the activation energy for oxidative addition between a transition metal and the C—O bond of an acylated phenol derivative would be fairly high. Since fused aromatic systems are known to be activated toward oxidative addition (see, e.g. Tobisu et al., *Angew. Chem. Int. Ed.* 2008, 47, 4866-4869; Lahti et al., *J. Org. Chem.* 1988, 53, 4590-4593; Cyranski et al., *Tetrahedron* 1998, 54, 14919-14924), a 1-naphthol derivative was first examined.

After a survey of various reaction parameters (e.g., choice of metal, ligand, solvent, base, additives, and temperature), catalyst systems were identified that facilitate the desired cross-coupling reactions. FIG. 2 provides a schematic of an embodiment of this system. Under optimal conditions (i.e., NiCl$_2$(PCy$_3$)$_2$ (5 mol %) and K$_3$PO$_4$ (4.5 equiv) in toluene at 80° C.), coupling of naphthyl pivalate 1 and phenylboronic acid (2a) afforded biaryl product 3a in 92% yield (FIG. 2, entry 1). Notably, the much more commonly used d$^8$ transition metal, palladium, was not readily effective at promoting the desired transformation, despite a comprehensive ligand survey. The success of a Ni catalyst is beneficial from a cost perspective because Ni is substantially cheaper than Pd, which is considered a precious metal (see, e.g. Keefe, J. C. AMMTIAC Quarterly 2007, 2, 9-14). The Ni-complex of choice, NiCl$_2$(PCy$_3$)$_2$ is commercially available from Strem Chemicals (Strem Chemicals Inc., Catalog # 28-0091), or can be prepared in one step from simple starting materials (see, e.g. Stone et al., Inorg. Chim. Acta 1970, 5, 434-438; Barnett, K. J. Chem. Educ. 1974, 51, 422-423; and Zim et al., Org. Lett. 2001, 3, 3049-3051). Furthermore, this Ni(II) precatalyst, which is thought to undergo in situ reduction to Ni(0) by excess boronic acid (see, e.g. Zim et al., Org. Lett. 2001, 3, 3049-3051), shows marked stability to air. Therefore, embodiments of the invention can be carried out on the benchtop rather than in a glovebox, thereby circumventing a common limitation of related Ni(0) processes (see, e.g. Tang et al., J. Am. Chem. Soc. 2004, 126, 3058-3059; and Tobisu et al., Angew. Chem. Int. Ed. 2008).

Embodiments of the invention can utilize a variety of chemical compounds in cross-coupling reactions. For example, as shown in Table 1 of FIG. 2, a range of arylboronic acids participate as partners in the Ni-catalyzed cross-coupling of naphthyl pivalate 1. Substitution is tolerated at the p, m, and o-positions as demonstrated by the coupling of tolyl substrates 2b-d (entries 2-4 in Table 1 of FIG. 2), respectively, although the o-substituted substrate (entry 4) requires elevated temperatures for modest success. Similarly, electron-deficient boronic acid 2e cross-couples at 120° C. to afford 3e in 82% yield (entry 5). Electron-rich substrate, 2f, bearing a p-methoxy substituent was also a competent cross-coupling partner (entry 6).

In another embodiment of the invention, a powerful one-pot process to access biaryl adducts directly from 1-naphthol has been developed. The procedure for this transformation involves in situ acylation of 1-naphthol with PivCl and K$_3$PO$_4$, followed by introduction of the appropriate boronic acid. For example, the one-pot acylation/cross-coupling sequence involving 1-naphthol and boronic acid 2f afforded biaryl adduct 3f in 86% isolated yield (Table 1 of FIG. 2, entry 7). To the best of our knowledge, this is the first example of a phenol cross-coupling that does not require isolation of a derivative that is activated toward oxidative addition.

The scope and efficiency of embodiments of the invention was demonstrated by varying the aryl pivalate component (Table 2 of FIG. 2). Cross-coupling of phenylboronic acid (2a) with the naphthyl pivalate substrate derived from 2-naphthol proceeded in 91% yield (entry 1 in Table 2 of FIG. 2). In addition, the reaction proved tolerant of an electron-withdrawing group (—CO$_2$Me, entry 2) and an electron-donating group (—OMe, entry 3) on the naphthyl ring. Given the importance of heterocycles in medicine, a heterocyclic pivalate substrate was tested in the cross-coupling reaction. In this embodiment of the invention, the Suzuki-Miyaura coupling of a substrate derived from N-Me-2-hydroxycarbazole proceeded in 82% yield (entry 4). In yet another embodiment of the invention, a vinyl pivalate derived from tetralone was found to be a suitable cross-coupling partner (entry 5).

Another advantage of using of pivalates in embodiments of the invention is their ability to direct the installation of functional groups onto an aromatic ring. A demonstration of this is highlighted in Scheme 2 in FIG. 3A, where naphthyl pivalate 1 was selectively brominated at C4 to afford bromopivalate 4 in 84% yield. The bulkiness of the pivalate group is thought to prevent the formation of ortho-brominated products. Postulating that the pivalate functional group of 4 would not be reactive toward Pd(0), orthogonal cross-coupling reactions of the bromide and pivalate groups were attempted. In the first cross-coupling, treatment of substrate 4 with indolylboronic ester 5 under Pd-catalysis led to the selective reaction of the aryl bromide to afford biaryl product 6, with the robust pivalate group remaining intact, despite the harsh basic conditions employed (i.e., aqueous K$_3$PO$_4$, 90° C.). Next, aryl pivalate 6 underwent smooth cross-coupling under nickel-catalyzed conditions to afford triaryl product 7 in 90% yield. It is notable that the indole heterocycle, which is prevalent in over 10,000 bioactive molecules to date, is tolerated under these reaction conditions.

Embodiments of the invention can use non-fused aryl pivalates in Suzuki-Miyaura reactions. Although it was anticipated that the cross-coupling of these non-activated substrates would be extremely challenging (see, e.g. Lahti et al., J. Org. Chem. 1988, 53, 4590-4593; and Cyranski et al., Tetrahedron 1998, 54, 14919-14924. Tobisu et al., Angew. Chem. Int. Ed. 2008, 47, 4866-4869), the desired reaction was demonstrated following the methods disclosed herein. For example, in a unoptimized process, coupling of electron-rich pivalate 8 with phenylboronic acid (2a) afforded biaryl adduct 9 in 60% isolated yield, with the remaining mass correlating to p-methoxyphenol (Scheme 3 in FIG. 3B). Related pivalate substrates that do not possess a p-methoxy group also react to provide biaryl products in slightly higher yields.

The studies disclosed herein reveal that ester- and methoxy-containing substrates undergo cross-coupling (Table 2 of FIG. 2, entries 2 and 3). Following the disclosure provided herein, one can observe the scope of the Suzuki-Miyaura coupling of aryl pivalates. For example, an assortment of 2,6-disubstituted naphthyl pivalates bearing either an electron-donating or an electron-withdrawing group can be prepared (FIG. 3C). Each of these substrates can be accessible by acylation of the corresponding hydroxyl derivatives, all of which are known, although most are also commercially available. These substrates can be subjected to the Ni-catalyzed cross-coupling conditions disclosed herein to demonstrate the power of this methodology. In addition, a variety of heterocyclic aryl pivalates can be examined in the coupling reactions disclosed herein. Substrates 10-13 (FIG. 3C) are good targets as each is readily accessible in one-step process from its commercially available non-pivalated precursor. By cross-coupling these substrates, one can quickly gauge the extent to which nitrogen-, oxygen-, and sulfur-containing heterocycles are tolerated in the disclosed methodology.

One aspect of the pivalate cross-coupling methodology disclosed herein involves the Suzuki-Miyaura coupling of non-fused aromatic substrates. As described earlier, the yields for this class of substrates are approximately 60%, with all remaining mass correlating to hydrolyzed starting material. Thus, one can carry out experiments to optimize the cross-coupling of non-fused aryl substrates (8, 14, 15a-c, FIG. 3D). Several parameters such as solvent, temperature, and base can be varied to evaluate condition parameters. In addition, one can investigate the effect of various additives, such as simple salts (e.g., LiBr), which have been used to accelerate oxidative addition in cross-coupling reactions (see, e.g. Lipshutz et al., Tetrahedron 2000, 56, 2139-2144). Finally, a number of other ligand scaffolds that have been useful for cross-coupling electron-rich substrates, including bidentate diamines and phosphines, can readily be examined to determine their properties in the systems disclosed herein (see, e.g. Negishi et al., *Acc. Chem. Res.* 1982, 15, 340-348. b) *Metal-Catalyzed Cross-Coupling Reactions*; Diedrich, F., Meijere, A., Eds.; Wiley-VCH: Weinheim, 2004; Vol. 2; Hassan et al., *Chem. Rev.* 2002, 102, 1359-1469; *Topics in Current Chemistry*; Miyaura, N., Ed.; Vol. 219; Springer-Verlag: New York, 2002; Corbet et al., *Rev.* 2006, 106, 2651-2710; and Negishi, *Bull. Chem. Soc. Jpn.* 2007, 80, 233-257).

As the oxidative addition into the aryl C—O bonds of aryl pivalates has been demonstrated, one can observe how other substrates undergo oxidative addition, and subsequent cross-coupling, under Ni-catalyzed conditions. For example, esters such as isobutyrates 16, benzoates 17, and acetates 18 can be examined following the disclosed methodology (see, e.g. FIG. 3E). These substrates, particularly 20, may undergo competitive hydrolysis under Suzuki-Miyaura conditions. However, given the potential cost benefit to using acetates as cross-coupling partners (readily prepared from Ac$_2$O or AcCl), effort to effect the cross-coupling of aryl acetates are reasonable. Additionally, aryl carbonates (19), carbamates (20), phosphates (21), and sulfamates (22) may participate in cross-coupling reactions under the methodologies disclosed herein. The fact that carbamates, phosphates, and sulfamates all undergo cross-coupling using the nickel-catalyzed reaction conditions provides evidence that these methods are broadly applicable to a variety of compounds. Similarly, aryl substrates of these types have never been employed in the Suzuki-Miyaura reaction. Such species are readily prepared in the laboratory and show reasonable stability to hydrolysis (see, e.g. Greene, T. W.; Wuts, P. G. M. *Greene's Protective Groups in Organic Synthesis*; 4th ed.; John Wiley & Sons, Inc.: New Jersey, 2007). In contrast to more expensive triflates, the corresponding carbonates, carbamates, phosphates, and sulfamates can serve as directing groups for ortho-metallation reactions, an extremely useful tactic for synthesizing substituted arenes (see, e.g. Lahti et al., *J. Org. Chem.* 1988, 53, 4590-4593. b) Cyranski et al., *Tetrahedron* 1998, 54, 14919-14924; and Macklin et al., *Org. Lett.* 2005, 7, 2519-2522).

Further aspects of embodiments of the invention are disclosed in the following examples.

EXAMPLES

Methods and materials for practicing embodiments of the invention as discussed below have also been published in the Journal of the American Chemical Society. These publications are: Quasdorf et al., *J. Am. Chem. Soc.*, 2008, 130 (44), pp 14422-14423; and Quasdorf et al., *J. Am. Chem. Soc.*, 2009, 131 (49), pp 17748-17749, the entire contents of which (e.g. including supplementary materials which are available via JACS online) are incorporated herein in their entirety Example 1

Cross-Coupling Reactions of Aryl Pivalates with Boronic Acids

As discussed in detail below, a highly efficient cross-coupling of acylated phenol derivatives has been achieved. In the presence of an air-stable Ni(II) complex, readily accessible aryl pivalates participate in the Suzuki-Miyaura coupling with arylboronic acids. These processes have a number of highly desirable features. For example, embodiments of the processes are tolerant of considerable variation in each of the cross-coupling components. Moreover, embodiments of the processes allow for one-pot acylation/cross-coupling sequences such as the ones disclosed herein. In addition, the use of an aryl pivalate as a directing group has also been demonstrated, along with the ability to sequentially cross-couple an aryl bromide followed by an aryl pivalate.

As is known in the art, transition metal-catalyzed cross-coupling reactions have emerged as one of the most powerful methods for constructing carbon-carbon (C—C) and carbon-heteroatom (C—X) bonds. Whereas methodologies for the cross-coupling of aryl halides have significantly improved in the past decade, less progress has been made toward the coupling of the corresponding phenol derivatives (see, e.g. *Metal-Catalyzed Cross-Coupling Reactions*; Diedrich, F., Meijere, A., Eds.; Wiley-VCH: Weinheim, 2004; Hassan et al., *Chem. Rev.* 2002, 102, 1359-1469; *Topics in Current Chemistry*; Miyaura, N., Ed.; Vol. 219; Springer-Verlag: New York, 2002; Corbet et al., *Chem. Rev.* 2006, 106, 2651-2710; Negishi, E. *Bull. Chem. Soc. Jpn.* 2007, 80, 233-257; and Littke, A. F.; Fu, G. C. *Angew. Chem. Int. Ed.* 2002, 41, 4176-4211). Given that many phenol compounds are cheap and readily available, and that oxygenation can be used to direct the installation of functional groups on an aromatic ring, practical methods that allow for the cross-coupling of phenol derivatives are extremely attractive.

Of the known methods for cross-coupling phenol derivatives, there are no examples that utilize simple O-acylated phenols (see, e.g. Zim et al., Org. Lett. 2001, 3, 3049-3051; Tang, Z.; Hu, Q. J. Am. Chem. Soc. 2004, 126, 3058-3059; Percec et al., J. Org. Chem. 2004, 69, 3447-3452; Zhang et al., J. Org. Chem. 2007, 72, 9346-9349; Munday et al., J. Am. Chem. Soc. 2008, 130, 2754-2755; Tobisu et al., Angew. Chem. Int. Ed. 2008, 47, 4866-4869). Of the known methods for phenol coupling, the most common involves formation and reaction of the corresponding aryl triflates. However, these species are somewhat costly to prepare, unable to serve as directing groups, and are susceptible to base-promoted hydrolysis. Aryl mesylates and tosylates can also be utilized, although their utility does not yet appear to be general. For unsuccessful attempts to effect the cross-coupling of O-acetylated phenols using Ni-catalysis, see: Guan et al., Chem. Commun. 2008, 1437-1439.

Efficient processes cross-coupling phenol derivatives (e.g. ones having yields of at least 25%) are of great value, given that O-acylated phenols are: exceedingly simple to prepare; among the most affordable phenol derivatives available; stable to a variety of reaction conditions; and able to direct the installation of other functional groups onto an aromatic ring. Furthermore, such cross-couplings would presumably begin by the selective oxidative addition of a metal into the aryl C—O bond of the O-acylated phenol, a transformation that has never been achieved (for the insertion of Ni(0) into the acryl C—O bond of acylated phenols, see: Yamamoto et al., *J. Am. Chem. Soc.* 1980, 102, 3758-3764). Below the first cross-coupling reactions of O-acylated phenol derivatives, involving the Ni-catalyzed reaction of aryl pivalates are described.

Of the vast array of cross-coupling reactions known, Suzuki-Miyaura couplings were considered because of the numerous advantages that pertain to using boronic acids (i.e., low toxicity, wide availability, stability to water and air, and high functional group tolerance). See, e.g.*Metal-Catalyzed Cross-Coupling Reactions*; Diedrich, F., Meijere, A., Eds.; Wiley-VCH: Weinheim, 2004; Hassan et al., *Chem. Rev.* 2002, 102, 1359-1469; *Topics in Current Chemistry*; Miyaura, N., Ed.; Vol. 219; Springer-Verlag: New York, 2002; Corbet et al., *Chem. Rev.* 2006, 106, 2651-2710; Negishi, E. *Bull. Chem. Soc. Jpn.* 2007, 80, 233-257; and Littke, A. F.; Fu, G. C. *Angew. Chem. Int. Ed.* 2002, 41, 4176-4211; Miyaura, N.; Suzuki, A. *Chem. Rev.* 1995, 95, 2457-2483; Suzuki, A. *Chem. Commun.* 2005, 4759-4763; and Doucet, H. *Eur. J. Org. Chem.* 2008, 2013-2030. Several challenges, however, were apparent from the outset. For example, certain O-acylated phenol substrates can be prone to hydrolysis under typical Suzuki-Miyaura conditions involving strong base. Thus, robust pivalate esters (—OC(O)CMe$_3$) were selected as the acylated phenol derivatives of choice. In addition, it was postulated that the activation energy for oxidative addition between a transition metal and the aryl C—O bond of an acylated phenol derivative would be fairly high. Since fused aromatic systems are generally activated toward oxidative addition, a naphthol derivative was first examined (see, e.g. *Metal-Catalyzed Cross-Coupling Reactions*; Diederich, F., Meijere, A., Eds.; Wiley-VCH: Weinheim, 2004; and Tobisu et al., Angew. Chem. Int. Ed. 2008, 47, 4866-4869).

An extensive survey of various reaction parameters (e.g., choice of metal, ligand, solvent, base, additives, and temperature) led to the identification of a catalyst system that facilitates the desired cross-coupling efficiencies. Under optimal conditions (i.e., NiCl$_2$(PCy$_3$)$_2$ (5 mol %) and K$_3$PO$_4$ (4.5 equiv) in toluene at 80° C.), coupling of naphthyl pivalate 1 and phenylboronic acid (2a) afforded biaryl product 3a in 92% yield. The Ni(II) precatalyst of choice is readily available and also shows marked stability to air. Therefore, all reactions can be routinely carried out on the bench-top rather than in a glovebox, thereby circumventing a common limitation of related Ni(0) processes.

The scope of this methodology was demonstrated by varying the aryl pivalate component. Cross-coupling of p-methoxyphenylboronic acid with a pivalate derivative of 2-naphthol proceeded in 92% yield. In addition, the reaction proved tolerant of an electron-withdrawing group (—CO$_2$Me) and an electron-donating group (—OMe) on the naphthyl ring. The corresponding reactions of non-fused aryl pivalates proved more challenging. Nonetheless, employing additional equivalents of boronic acid and increasing catalyst loading to 10 mol %, significantly improved the yields of cross-coupled products. For instance, p- and o-tolyl pivalates afforded products in 65% and 79% yields, respectively. A non-fused aromatic substrate bearing a p-methoxy substituent also participated in the cross-coupling reaction. Finally, a substrate derived from N-methyl-2-hydroxycarbazole underwent smooth cross-coupling, as did a vinyl pivalate derived from tetralone.

A range of arylboronic acids are found to participate in the Ni-catalyzed cross-coupling of naphthyl pivalate. Cross-coupling of electron-rich boronic acid, bearing a p-methoxy substituent, furnished biaryl adduct in 95% yield. Electron-deficient boronic acid can also be utilized in the desired cross-coupling reaction. Finally, Me-substitution is tolerated at the p, m, and o-positions as demonstrated by the coupling of substrates, respectively, although the o-substituted substrate requires elevated temperatures and proceeds in modest yield.

One-pot acylation/cross-coupling sequence and orthogonal cross-coupling reactions were demonstrated. This highlights two unprecedented and powerful variations of the cross-coupling methods described herein. As pivalylation protocols typically proceed quantitatively and with minimal byproduct formation, it was hypothesized that a one-pot acylation/cross-coupling sequence of phenol derivatives could be possible. Gratifyingly, the efforts to achieve the one-pot conversion of 1-naphthol to biaryl adduct were successful, affording the desired product in 86% yield. Next, to demonstrate the directing ability of aryl pivalates, naphthyl pivalate was selectively brominated at C4 to afford bromopivalate in 84% yield. Postulating that the pivalate functional group would not be reactive toward Pd(0), orthogonal cross-coupling reactions of the bromide and pivalate groups were attempted. In the first cross-coupling, treatment of substrate with indolylboronic ester under Pd-catalysis led to the selective reaction of the aryl bromide to afford biaryl product, with the robust pivalate group remaining intact, despite the harsh basic conditions employed (i.e., aqueous K$_3$PO$_4$, 90° C.). Next, aryl pivalate underwent smooth cross-coupling under these nickel-catalyzed conditions to afford triaryl product in 88% yield.

In summary, this example discloses working examples of efficient cross-coupling reactions of O-acylated phenol derivatives. The method described relies on the use of a readily available, air-stable Ni(II) complex to facilitate the Suzuki-Miyaura coupling of aryl pivalates. In addition, a one-pot acylation/cross-coupling sequence has been developed. Moreover, the potential to utilize an aryl pivalate as a directing group has been demonstrated, along with the ability to sequentially cross-couple an aryl bromide followed by an aryl pivalate. Studies aimed at probing mechanistic aspects of these findings are currently underway.

Example 2

Suzuki-Miyaura Coupling of Aryl Carbamates, Carbonates, and Sulfamates

As discussed in detail below, a highly efficient Suzuki-Miyaura cross-coupling of carbamates, carbonates, and sulfamates has been achieved. The method presented provides a powerful means to use simple derivatives of phenol as precursors to polysubstituted aromatic compounds, as exemplified by a concise synthesis of the anti-inflammatory drug flurbiprofen.

Transition metal-catalyzed cross-coupling reactions play a vital role in modern synthetic chemistry (see, e.g. *Metal-Catalyzed Cross-Coupling Reactions*; Diederich, F., Meijere, A., Eds.; Wiley-VCH: Weinheim, 2004; Hassan et al., *Chem. Rev.* 2002, 102, 1359-1469; *Topics in Current Chemistry*; Miyaura, N., Ed.; Vol. 219; Springer-Verlag: New York, 2002; Corbet, J.; Mignani, G. *Chem. Rev.* 2006, 106, 2651-2710; and Negishi, E. *Bull. Chem. Soc. Jpn.* 2007, 80, 233-257). Although cross-couplings of aryl halides and triflates are most common, recent studies such as those disclosed in Example 1 above have demonstrated the successful cross-coupling of simple and affordable phenolic derivatives. In 2008, notable achievements in this area include the Suzuki-Miyaura coupling of electron deficient aryl methyl ethers by Chatani (see Tobisu et al., *Angew. Chem. Int. Ed.* 2008, 47, 4866-4869), and the Suzuki-Miyaura coupling of aryl pivalates (see, Tobisu et al., *Angew. Chem. Int. Ed.* 2009, 48, 3565-3568; Goosen et al., *Angew. Chem. Int. Ed.* 2009, 48, 3569-3571; and Knochel et al., *Synfacts* 2009, 2, 2009), which was reported simultaneously by us and the group of Shi (see Shi, Z.J. *J. Am. Chem. Soc.* 2008, 130, 14468-14470). A conceptual advantage of these technologies, compared to methodologies involving halides and sulfamates, is the potential to direct the installation of other functional groups onto an aromatic ring prior to cross-coupling (see FIG. 5A). In practice, however, the ability to use methyl ethers (R=Me) and pivalates (R=OC(O)CMe$_3$) in this sense is somewhat limited. Given the importance of polyfunctionalized aromatics in medicine, ligands for catalysis, and materials chemistry, attempts were made to address this problem. In this Example, the efficient Suzuki-Miyaura couplings of aryl carbamates, carbonates, and sulfamates are described. As one illustration of the value of this methodology (see, e.g. FIG. 5E), a concise synthesis of the anti-inflammatory drug flurbiprofen is disclosed. For reviews of flurbiprofen, see, e.g. Richy et al., *Int. J. Clin. Pract.* 2007, 61, 1396-1406; and Kumar et al., *Asian J. Chem.* 2004, 16, 558-562.

Of the potential phenolic derivatives to be studied, aryl carbamates and sulfamates were considered ideal because of their ready availability and pronounced stability to a variety of reaction conditions. Furthermore, these substrates can be used to direct the installation of functional groups at both the ortho and para positions (via ortho-lithiation chemistry pioneered by Snieckus and electrophilic aromatic substitution, respectively, see, e.g. Snieckus, V. *Chem. Rev.* 1990, 90, 879-933; Macklin, T. K.; Snieckus, V. *Org. Lett.* 2005, 7, 2519-2522; and Smith, M. B.; March, J. *March's Advanced Organic Chemistry*; 6th ed.; John Wiley & Sons, Inc.: New Jersey, 2007; p 668). Although nickel-catalyzed Kumada couplings of these substrates have been documented, cross-coupling under milder, more attractive Suzuki-Miyaura conditions have not been reported (see, e.g. Macklin, T. K.; Snieckus, V. *Org. Lett.* 2005; Sengupta et al., V. *J. Org. Chem.* 1992, 57, 4066-4068; Dallaire et al., *Org. Synth.* 2002, 78, 42; Yoshikai et al., *J. Am. Chem. Soc.* 2009, 131, 9590-9599; and Wehn, P. M.; Du Bois, J. *Org. Lett.* 2005, 21, 4685-4688). Of note, the oxidative addition of a metal into the aryl C—O bond of an aryl carbamate or sulfamate presents a considerable challenge. Despite this difficulty, it was found that the Suzuki-Miyaura coupling of aryl carbamates with aryl boronic acids proceeds in the presence of $NiCl_2(PCy_3)_2$, $K_3PO_4$, and heat, with toluene as solvent (Table 1 of FIG. 5C). That $NiCl_2(PCy_3)_2$ could be used to facilitate the desired transformation is advantageous, as this readily available complex shows marked stability to air and water, and can be used on the bench-top rather than in a glovebox. $NiCl_2(PCy_3)_2$, is commercially available from Strem Chemicals Inc. (catalog #28-0091), or can be prepared in multigram quantities following a simple one-step protocol (see, Stone, P. J.; Dori, Z. *Inorg. Chim. Acta* 1970, 5, 434-438; and Barnett, K. W. *J. Chem. Educ.* 1974, 51, 422-423). In the presence of excess arylboronic acid, $NiCl_2(PCy_3)_2$ is thought to undergo reduction to an active Ni(0) catalyst.

Table 1 in FIG. 5C shows the cross-coupling of aryl carbamates and carbonates with arylboronic acids 2a or 2b ([a] Conditions: $NiCl_2(PCy_3)_2$ (10 mol %), $ArB(OH)_2$ (4 equiv), $K_3PO_4$ (7.2 equiv), toluene (0.3 M), 130° C. for 24 h. [b] Conditions: $NiCl_2(PCy_3)_2$ (5mol %), $ArB(OH)_2$ (2.5 equiv), $K_3PO_4$ (4.5 equiv), toluene (0.3 M), 110° C., 24 h. [c] Isolated yields). As shown in FIG. 5C, the carbamate derivative of 1-naphthol could be converted to the desired biaryl product at 110° C. with 5 mol % Ni complex (entry 1). However, the yield improved substantially by carrying out the reaction at higher temperatures with increased catalyst loading (entry 2). 2-Naphthol derivatives could also be coupled under these conditions (entries 3 and 4). In addition, the reaction proved tolerant of an electron-withdrawing group (—$CO_2Me$, entry 4) and an electron-donating group (—OMe, entry 5) on the naphthyl ring. The corresponding reactions of non-fused aryl carbamates proved more challenging. Nonetheless, carbamates derived from phenol and p-methoxyphenol could be converted to the corresponding cross-coupled products, albeit in modest yields (entries 6 and 7). Aryl t-butylcarbonates were also deemed suitable cross-coupling partners (entries 8-10). Interestingly, the carbonate congener of 2-naphthol delivered the cross-coupled product in significantly higher yield compared to the corresponding carbamate (entry 9 and entry 3). Table 2 in FIG. 5D shows the cross-coupling of aryl sulfamates (Conditions: $NiCl_2(PCy_3)_2$ (5 mol %), $ArB(OH)_2$ (2.5 equiv), $K_3PO_4$ (4.5 equiv), toluene (0.3 M), 110° C., 24 h. [b] Isolated yields. [c] Conditions: $NiCl_2(PCy_3)_2$ (10 mol %), $ArB(OH)_2$ (4 equiv), $K_3PO_4$ (7.2 equiv), toluene (0.3 M), 130° C., 24 h.). As shown in Table 2, aryl sulfamates serve as superior coupling partners in the Ni-catalyzed Suzuki-Miyaura reaction. Both naphthyl and non-fused aromatic substrates could be converted to biaryl products in excellent yield (entries 1-11). Electron-withdrawing (entries 2 and 9) and electron-donating groups were tolerated (entries 3, 10, and 11). In addition to para, meta, and ortho-methyl substituents (entries 5-7), a sterically congested 2,6-disubstituted substrate also participated in the desired cross-coupling process (entry 8). A heteroaromatic sulfamate (entry 12) and a vinyl sulfamate (entry 13) proved to be competent substrates. Finally, a range of o-substituted sulfamates, prepared by o-lithiation/functionalization of phenyl dimethylsulfamate, underwent smooth cross-coupling in excellent yields (entries 14-17).

To further probe the scope and utility of the sulfamate cross-coupling methodology, a synthesis of the anti-inflammatory drug flurbiprofen was performed (see FIG. 5E). As shown in FIG. 5E, boronic acid 3, derived from o-lithiation/borylation of phenyl dimethylsulfamate, was fluorinated using the conditions described by Furuya and Ritter to provide fluorosulfamate 4 (see, e.g. Furuya, T.; Ritter, T. *Org. Lett.* 2009, 11, 2860-2863). Selective iodination of 4 para to the sulfamate furnished 5 in 64% yield. Of note, both the fluoride and sulfamate of 5 were deemed unreactive toward Pd(0). As the aryl iodide displayed orthogonal reactivity, a site-selective enolate coupling was carried out to install the necessary propionate side chain. Whereas enolate coupling of aryl iodide 5 under Buchwald's Pd-based conditions was feasible, higher yields of 6 were obtained using a Ni-catalyzed variant (see, e.g. Moradi et al., *J. Am. Chem. Soc.* 2001, 123, 7996-8002; and Durandetti et al., *Tetrahedron* 2007, 63, 1146-1153). Although the sulfamate was not disturbed in this process, exposure of 6 to the Ni-catalyzed Suzuki-Miyaura conditions facilitated the key sulfamate cross-coupling. Acid-mediated hydrolysis furnished flurbiprofen (1) in 84% yield, over the two steps. It should be emphasized that the aryl fluoride of 6 was chemically inert under the nickel-catalyzed cross-coupling conditions (For nickel-catalyzed Kumada and Suzuki-Miyaura couplings of aryl fluorides, see: Yoshikai et al., *J. Am. Chem. Soc.* 2005, 127, 17978-17979; Dankwardt, J. W. *J. Organomet. Chem.* 2005, 690, 932-938; and Schaub et al., *J. Am. Chem. Soc.* 2006, 128, 15964-15965).

In summary, efficient processes for Suzuki-Miyaura coupling reactions of aryl carbamates, carbonates, and sulfamates are described. Embodiments of the method rely on the use of a readily available, air-stable Ni(II) complex to facilitate the desired transformations. Furthermore, the technology presented herein allows for the installation of multiple functional groups onto an aromatic ring prior to the cross-coupling event, as demonstrated by a concise synthesis of the anti-inflammatory drug flurbiprofen.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method for making a cross-coupled compound comprising:
   combining together:
   (1) an organoboron compound consisting essentially of an organoboronic acid, a diorganoborinic acid, a organoboronate ester, an organoboroxine, a organotrialkoxyborate, an organotrifluoroborate, an organotrihydroxyborate, a tetraorganoborate, a triorganoborane, an alkylborane or a tetrafluoroborate compound;
   (2) an aryl alcohol derivative having the structure:

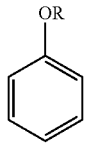

wherein R consists essentially of
   an acyl moiety;
   a carbamoyl moiety;
   a carboxyl moiety;
   a sulfamoyl moiety; or
   a phosphoryl moiety; and
   (3) a transition metal catalyst, wherein the transition metallic catalyst comprises nickel or palladium;
   wherein (1), (2) and (3) are combined so as to allow a cross-coupling reaction that results in the formation of the cross-coupled compound in a yield of at least 25%;
   so that the cross-coupled compound is made.

2. The method of claim 1, wherein the cross-coupling reaction results in the formation of the cross-coupled compound in a yield of at least 50%.

3. The method of claim 1, wherein the cross-coupled compound is formed from a one-pot synthesis.

4. The method of claim 1, wherein the transition metallic catalyst comprises nickel.

5. The method of claim 1, wherein the transition metal catalyst comprises an air stable Ni(II) precatalyst complex prior to its combination with (1) and (2).

6. The method of claim 1, wherein the transition metal catalyst is regenerated simultaneously with formation of the cross-coupled compound.

7. The method of claim 1, wherein the cross-coupled compound is formed via a Suzuki-Miyaura cross-coupling reaction.

8. A method for performing a Suzuki-Miyaura cross-coupling reaction comprising:
   combining together:
   (1) an organoboron compound consisting essentially of an organoboronic acid, a diorganoborinic acid, a organoboronate ester, an organoboroxine, a organotrialkoxyborate, an organotrifluoroborate, an organotrihydroxyborate, a tetraorganoborate, a triorganoborane, an alkylborane or a tetrafluoroborate compound;
   (2) an aryl alcohol derivative having the structure:

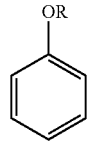

wherein R consists essentially of:
   an acyl moiety;
   a carbamoyl moiety;
   a carboxyl moiety;
   a sulfamoyl moiety; or
   a phosphoryl moiety; and
   (3) a transition metal catalyst, wherein the transition metallic catalyst comprises nickel or palladium;
   wherein (1), (2) and (3) are combined so as to allow:
   oxidative addition of the transition metal catalyst and generation of a first organo-transition metal species;
   reaction between the first organo-transition metal species and the organoboron compound and generation of a second organo-transition metal species; and
   reductive elimination of the second organo-transition metal species, regeneration of the transition metal catalyst and generation of a cross-coupled compound in a yield of at least 25%;
   so that a Suzuki-Miyaura cross-coupling reaction is performed.

9. The method of claim 8, wherein the reaction produces the cross-coupled compound in a yield of at least 50%.

10. The method of claim 8, wherein the organoboron compound comprises an arylboronic acid compound.

11. The method of claim 8, wherein the metallic catalyst comprises nickel and the organo-transition metal species comprises an organo-nickel species.

12. The method of claim 8, wherein the reaction is performed as a one-pot synthesis.

13. The method of claim 8, wherein the Suzuki-Miyaura cross-coupling reaction is not performed in a glovebox.

14. The method of claim 8, wherein the transition metal catalyst comprises an air stable Ni(II) precatalyst complex immediately prior to its combination with the organoboron compound and (2).

15. The method of claim 8, further comprising performing a base mediated hydrolysis on the cross-coupled compound.

16. The method of claim 15, wherein the cross-coupled compound is an intermediate in the synthesis of flurbiprofen.

* * * * *